United States Patent [19]
Haworth

[11] Patent Number: 5,219,338
[45] Date of Patent: Jun. 15, 1993

[54] SAFETY SYRINGE WITH COLLAPSIBLE NEEDLE GUARD

[76] Inventor: Warren D. Haworth, Rt. 1, Box 1607, Fort Gibson, Okla. 74434

[21] Appl. No.: 656,011

[22] Filed: Feb. 14, 1991

Related U.S. Application Data

[63] Continuation of Ser. No. 467,016, Jan. 18, 1990, abandoned.

[51] Int. Cl.⁵ ............................................. A61M 5/32
[52] U.S. Cl. ................................... 664/198; 604/263
[58] Field of Search ............... 604/110, 192, 198, 263

[56] References Cited

U.S. PATENT DOCUMENTS

| | | | |
|---|---|---|---|
| 3,134,380 | 5/1964 | Armao | 604/198 |
| 4,804,371 | 2/1989 | Vaillancourt | 604/198 |
| 4,846,809 | 7/1989 | Sims | 604/198 |
| 4,894,055 | 1/1990 | Sudnak | 604/198 |
| 4,911,694 | 3/1990 | Dolan | 604/198 |
| 4,915,697 | 4/1990 | DuPont | 604/192 |
| 4,927,416 | 5/1990 | Tankiel | 604/198 |
| 4,932,947 | 6/1990 | Cardwell | 604/198 |
| 4,943,281 | 7/1990 | Kothe | 604/192 |

*Primary Examiner*—John D. Yasko
*Assistant Examiner*—Alan J. Cermak
*Attorney, Agent, or Firm*—Head & Johnson

[57] ABSTRACT

A safety syringe having an elongated tubular barrel, a needle and a tubular protective sheath having one end affixed to the external surface of the barrel and normally encompassing the needle. The protective sheath has accordion-like circumferential pleats formed therein, the sheath normally extending over a substantial portion of the barrel and the needle to thereby prevent inadvertent contact of the needle with the user, the sheath being retractable to permit the needle to be used for subcutaneous dispensation of liquid contents from the barrel.

6 Claims, 2 Drawing Sheets

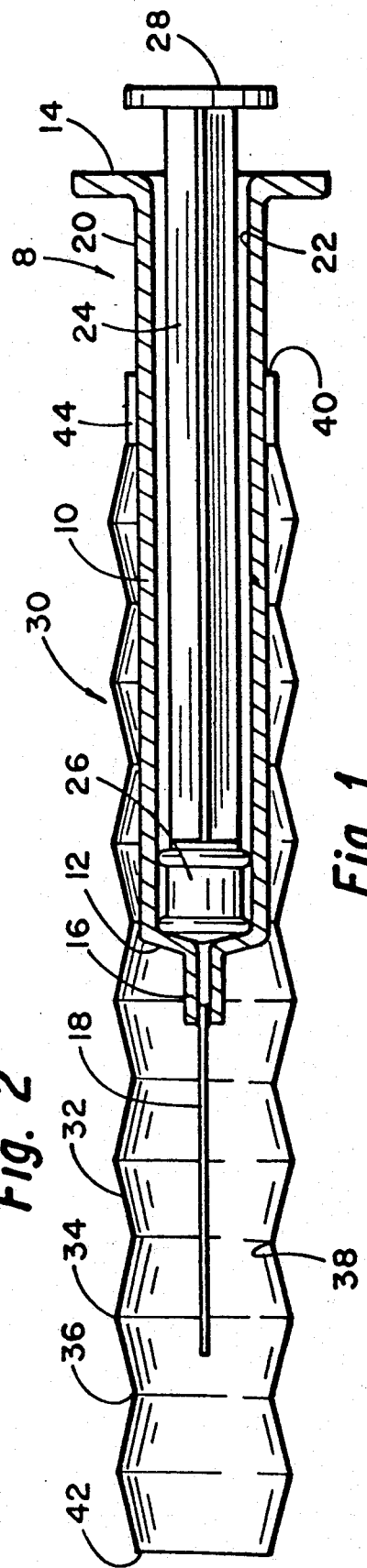
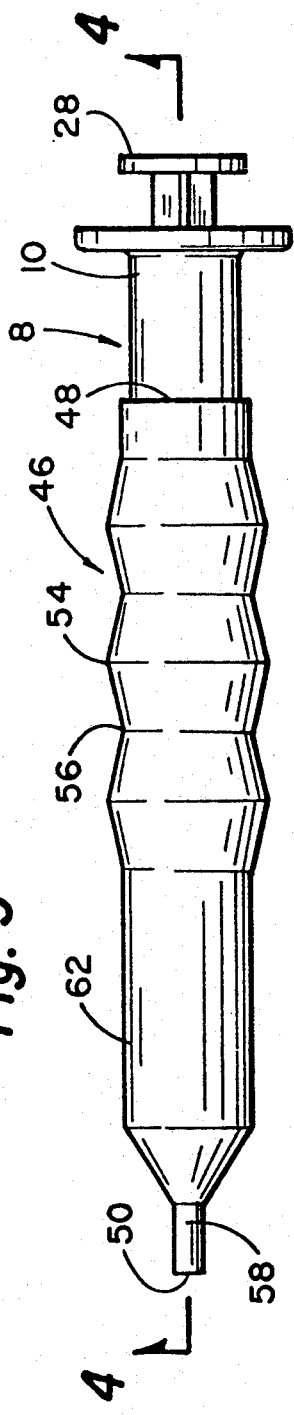
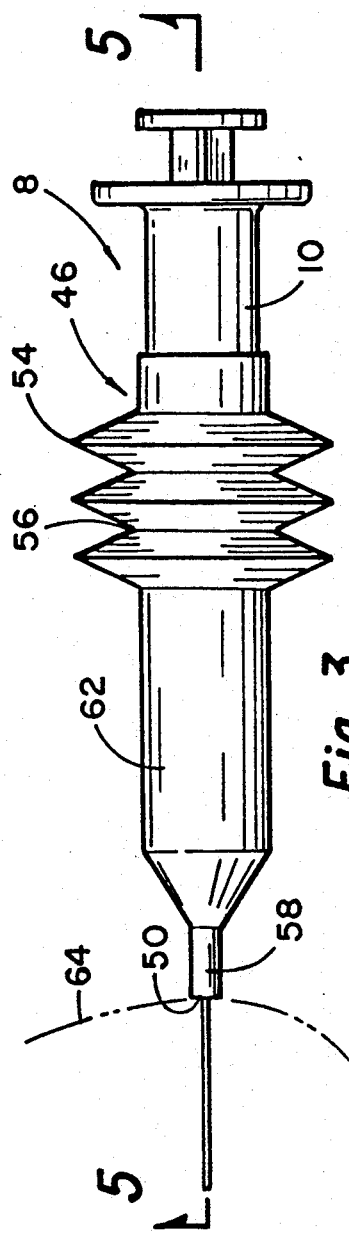

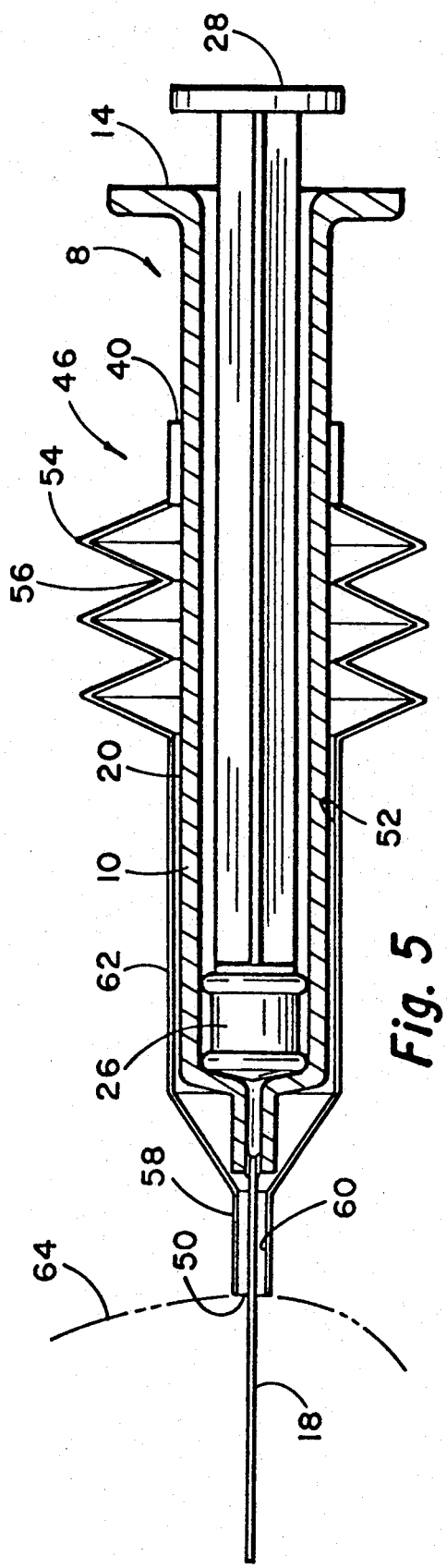
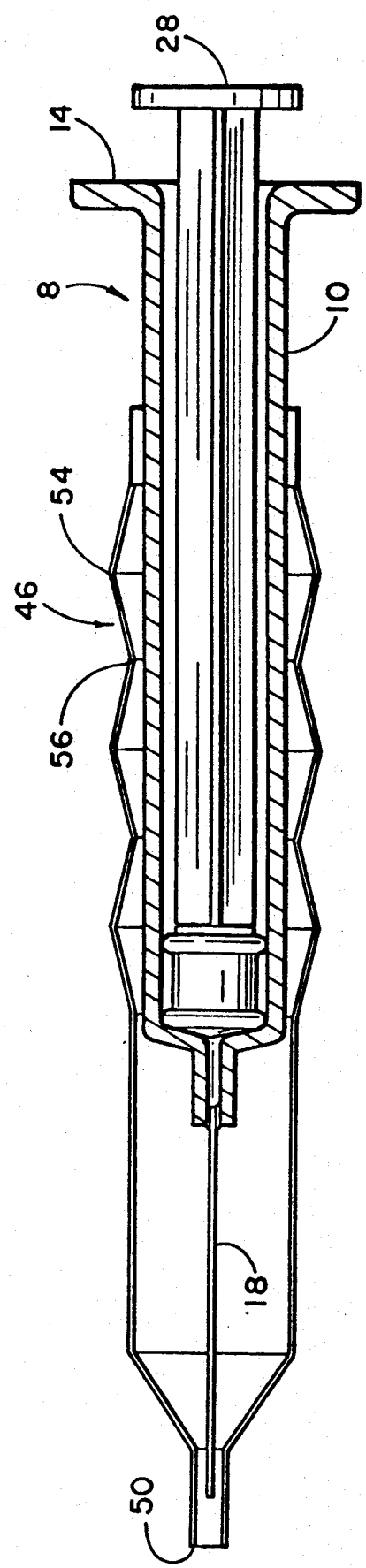

SAFETY SYRINGE WITH COLLAPSIBLE NEEDLE GUARD

This is a continuation of copending application Ser. No. 07/467,016 filed on Jan. 18, 1990, now abandoned.

SUMMARY OF THE DISCLOSURE

Syringes are frequently used by the medical profession for injecting liquids into patients. Syringes typically include a barrel having a needle extending therefrom and a plunger reciprocally positioned within the barrel. The syringe is used by first extending the needle underneath the skin of the patient and then the plunger is moved forward in the barrel to force fluid from the interior of the barrel, through the needle and into the patient.

Syringes are supplied by the manufacturer in sterilized condition. However, once a syringe has been used to inject fluid into a patient, the needle is exposed to the blood and other body fluids of the patient, and upon withdraw from the patient, has the possibility of carrying infection producing bodies thereon. A syringe, after it has been used to inject a patient, is a hazardous implement. If the patient is a carrier of disease such as AIDS, the needle is particularly dangerous, and if a doctor or nurse is accidentally penetrated by the needle after it has been used on a patient, the possibility exists for the transmission of an infectious disease, including AIDS.

The safety syringe of this disclosure provides a means of protecting the lower portion of a syringe and a needle from inadvertent contact with a doctor, nurse or other users of the syringe.

Others have provided protective devices for similar purposes, and for background reference to such devices, reference may be had to the following U.S. Pat. Nos.: 3,134,380; 4,804,372; 4,795,432; 4,804,371; 4,775,369; 4,772,272; 4,631,057; 4,664,654; 4,139,009; 4,762,516; 4,832,696; 2,935,067; 4,778,453 and 4,747,837.

In the first embodiment of the present disclosure a syringe has a barrel and, at one end thereof, a needle. The other end of the syringe is open and receives telescopically a plunger. When the plunger is advanced liquid within the barrel is forced through the needle. The needle may be permanently affixed to the syringe so that the syringe and needle are intended for one-time use and then discarded. This disclosure is not concerned with the details of the syringe or any improvements therein but with means of protecting the needle against inadvertent puncture of the skin of a doctor, nurse or other persons using the syringe on a patient.

Positioned on the external surface of the barrel of the syringe is a tubular protective sheath preferably formed of plastic. The tubular sheath has one end thereof secured to the outside of the barrel. The sheath, or at least a substantial portion of the length thereof, is provided with integral circumferential accordion-like pleats. The free end of the sheath extends normally beyond the end of the needle so that as long as the sheath is in its normal position, the needle is maintained within the sheath and the possibility of inadvertent contact with the needle is substantially non-existent.

To use the syringe, the sheath is retracted manually to expose the needle to permit the needle to be inserted into the skin of the patient. After the needle is inserted, manual force on the sheath can be removed, and upon removal of the needle from the skin of the patient, the sheath immediately and automatically extends to recover the needle. The needle is always covered against inadvertent contact except when the sheath is intentionally manually displaced to expose the needle.

In another embodiment of the disclosure, the sheath has, at the free end thereof, an integral reduced internal diameter portion which slidably receives the needle when the sheath is retracted to expose the needle.

A better understanding of the invention will be had by reference to the following description and claims, taken in conjunction with the attached drawings.

DESCRIPTION OF THE DRAWINGS

FIG. 1 is a cross-sectional elevational view of a basic embodiment of the disclosure, showing a syringe with the barrel thereof in cross-section and with a telescopic tubular sheath positioned on the syringe barrel.

FIG. 2 is an elevational external view of an alternate embodiment wherein the sheath has, at the free end thereof, an integral reduced diameter portion that slidably receives the needle. In the embodiment of FIG. 2, the sheath has circumferential pleats in a portion thereof, with the other portion of the sheath being of cylindrical-shape without pleats.

FIG. 3 is a view of the embodiment of FIG. 2 with the sheath retracted to expose the needle, such as for use in making a subcutaneous injection into a patient.

FIG. 4 is a cross-sectional view taken along the line 4—4 of FIG. 2 showing the embodiment of FIG. 2 in cross-section.

FIG. 5 is a cross-sectional view taken along the line of 5—5 of FIG. 3 showing, in cross-section, the sheath retracted.

DESCRIPTION OF THE PREFERRED EMBODIMENT

Referring to the drawings and first to FIG. 1, a basic embodiment of the disclosure is illustrated. A syringe barrel is indicated by the numeral 10, having a first or distal end 12 and second or proximal end 14. The distal end 12 of the barrel has an integral reduced diameter portion 16 that receives and retains a needle 18.

Barrel 10 has an external cylindrical surface 20 and an internal cylindrical surface 22. Received within the barrel is a plunger 24 and on the distal end of the plunger a piston 26 that slidably engages the barrel internal surface 22. The outer end of plunger 24 has a handle portion 28.

The syringe described to this point, including all elements numbered 10 through 28, is of standard construction and does not form a part of the novel features of this disclosure. A syringe can be manufactured in many different configurations, however, that illustrated is exemplary of syringes in common use at the present time, which typically have needle 18 permanently secured to the syringe with the intent that the syringe used for only one application and then discarded. The principles of this disclosure apply to a syringe of varying configurations, and that illustrated and described is for purposes of example only.

A serious concern of the users of syringes, such as doctors and nurses, is that after the syringe has been used for a subcutaneous injection and the needle withdrawn from a patient, the needle represents a hazardous element. The needle, after an injection, is a carrier of remnants of blood and body fluids of the person who has been injected with the needle, and, therefore, is a means of transmission of diseases. If the needle 18, after having been used, accidentally penetrates the skin of the doctor or nurse having made an injection of a patient using the syringe, the doctor or nurse is subject to being inoculated with any diseases carried by the needle. For this reason, it is important that means be provided to reduce the possibility of such inadvertent inoculation. For this purpose, a protective sheath, generally indicated by the numeral 30, is affixed to the syringe. The sheath is in the form of an elongated tubular member 32 that has a series of circumferential integral accordion-like pleats that provide alternate circumferential peaks 34 and valleys 36.

The diameter of the internal surface 38 of sheath 30 is greater than the external diameter 20 of the syringe barrel 10 so that the sheath is telescopic on the syringe barrel. The sheath has a proximal end 40 and a distal or free end 42. The distal end 42 is open, whereas the proximal end 40 has a reduced diameter integral portion 44 that snugly and fixedly is received on the external surface 20 of the syringe barrel.

The sheath 30 is configured so as to normally extend, as indicated in FIG. 1, covering the needle. When the syringe is to be used, the portion adjacent the syringe distal end 42 is moved toward the proximal end 40 by one hand of the user, exposing needle 18, while the other hand of the user supports the syringe and is positioned so that by use of thumb pressure on handle 28 the plunger 24 is moved to eject fluid through the needle. After the syringe has been used to insert into a patient, manual force on the syringe distal portion is removed. Sheath 30 returns automatically to the position as shown in FIG. 1, fully enclosing needle 18. Therefore, after the syringe has been used and withdrawn from a patient, the needle is automatically fully protected against inadvertent contact with the skin of a doctor, nurse or other person who has made use of the syringe.

An alternate embodiment of the disclosure is shown in FIGS. 2 through 5. In this embodiment, the syringe 8 is the same as has been described with reference to FIG. 1. The sheath, generally indicated by the numeral 46, is in many ways the same as the sheath 30 in FIG. 1 but with differences. Sheath 46 has a proximal end 48 and a distal end 50. The sheath is tubular with an internal circumferential surface 52 greater than the syringe barrel external cylindrical surface 20. Sheath 46, like sheath 30, has integral circumferential accordion-like pleats with peaks 54 and valleys 56 so that the sheath is telescopic with respect to the syringe barrel 10.

The portion of sheath 46 adjacent the distal end 50 is different from that of FIG. 1, that is, in the alternate embodiment, the portion adjacent the distal end has an integral reduced diameter portion 58 which is of short tubular length and has an internal diameter 60 substantially less than the internal diameter of syringe barrel 10, and it is sized to slidably receive needle 18.

The sheath 46 of the embodiment of FIGS. 2 through 5 further includes a cylindrical portion 62 adjacent the distal end 50 which does not contain pleats, so that in this embodiment, the pleats 54 and valleys 56 exist only over a portion of the length of the sheath.

FIGS. 3 and 5 show the sheath retracted to fully expose needle 82, such as when injecting it into the skin of a patient, the skin 64 being shown in dotted outline.

The embodiment of FIGS. 2 through 5 functions essentially the same as that of FIG. 1. When the syringe is to be used to make an injection, the user can, with one hand, retract the sheath to fully expose the needle 18 or the syringe may simply be moved against the patient so that the distal end 50 contacts the skin 64. The needle will then move through the outer tubular portion 58. When the needle is withdrawn from the patient, the sheath automatically extends out over the needle 18 to prevent inadvertent engagement of the needle with the user.

The disclosure provides an effective and yet easy to use system for increasing the safety of syringes. The plastic sheath can be inexpensively made, and the attachment thereof to existing syringes is easily accomplished. The telescopic sheath adds insignificantly to the cost of a disposable or throw away syringe. It provides protection of the needle prior to use of the syringe and shields the needle against inadvertent contact with the user after an injection.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A safety syringe comprising:
   an elongated tubular barrel having a proximal and a distal end and having a generally cylindrical external surface and having a needle retaining portion at the distal end;
   a plunger telescopically received within at least a portion of said tubular barrel and having one end extending beyond the barrel proximal end;
   a needle affixed to and extending from said barrel distal end; and
   a tubular protective sheath affixed at one end to the external surface of said barrel and surrounding at least a substantial portion of said barrel portion having said plunger and extending to normally encompass said needle, at least a substantial portion of the protective sheath having elastically resilient accordion-like circumferential pleats formed therein, the protective sheath having a proximal end affixed to said tubular barrel external surface and a distal end having an opening therein of at least sufficient internal dimension to telescopically envelop said needle, the distal end of said protective sheath being displaceable upon the application of external force toward said proximal end to overcome the elastically resilient action of said circumferential pleats and to at least partially compress said circumferential pleats surrounding said barrel portion having said plunger therein to expose said needle and in the absence of external displacing force to, at all times, envelop said needle.

2. A syringe according to claim 1 wherein said protective sheath is of substantially the same general diameter throughout the length thereof.

3. A syringe according to claim 2 wherein said accordion-like circumferential elastically resilient pleats extend substantially the full length of said protective sheath.

4. A syringe according to claim 1 wherein said protective sheath has, at said distal end thereof, an integral reduced internal and external diameter portion, the internal diameter of such portion being greater than the external diameter of said needle, the reduced diameter portion telescopically enveloping a portion of said needle.

5. A syringe according to claim 4 wherein said protective sheath has said integral accordion-like circumferential pleats in the portion thereof adjacent said proximal end and encompassing said barrel portion having said plunger therein and including a tubular non-pleated portion between said pleated portion and said integral reduced internal and external diameter needle receiving portion, the tubular non-pleated portion telescopically receiving said distal end portion of said barrel.

6. A syringe according to claim 1 wherein said protective sheath includes an integral reduced internal diameter portion at said proximal end, which portion non-slidably engages said barrel external surface.

* * * * *